United States Patent [19]

Wagenknecht

[11] Patent Number: 4,941,481
[45] Date of Patent: Jul. 17, 1990

[54] DEVICE FOR POSITIONING AND SECURING A PART HAVING CIRCULAR REGIONS

[75] Inventor: Marcel Wagenknecht, Le Ligon, Switzerland

[73] Assignee: Jaquet Orthopedie, S.A., Geneva, Switzerland

[21] Appl. No.: 935,416

[22] Filed: Nov. 26, 1986

[30] Foreign Application Priority Data

Nov. 29, 1985 [CH] Switzerland .................. 5119/85
Sep. 29, 1986 [CH] Switzerland .................. 3894/86

[51] Int. Cl.⁵ .................................. A61F 5/04
[52] U.S. Cl. ........................... 606/59; 403/90; 403/373
[58] Field of Search ............... 128/92Z W, 92Z, 346; 403/90, 344, 373; 101/D17

[56] References Cited

U.S. PATENT DOCUMENTS

| | | | |
|---|---|---|---|
| 675,106 | 5/1901 | Oberle | 403/90 |
| 973,319 | 10/1910 | Thunen et al. | 403/90 |
| 1,317,903 | 10/1919 | Whimster | 403/90 |
| 2,439,995 | 4/1948 | Thrailkill | 128/92 ZW |
| 3,691,788 | 9/1972 | Mazziotti | 403/90 |
| 3,841,769 | 10/1974 | Bowerman | 403/90 |
| 4,127,119 | 11/1978 | Kronner | 128/92 Z |
| 4,128,355 | 12/1978 | Leaf | 403/344 |
| 4,227,826 | 10/1980 | Conrad | 403/90 |
| 4,273,116 | 6/1981 | Chiquet | 128/92 Z |
| 4,299,212 | 11/1981 | Goudfooy | 128/92 ZW |
| 4,312,336 | 1/1982 | Danieletto et al. | 128/92 ZZ |
| 4,458,681 | 7/1984 | Hopkins | 128/346 |
| 4,600,000 | 7/1986 | Edwards | 128/92 Z |
| 4,616,949 | 10/1986 | Kellner | 403/344 |
| 4,620,533 | 11/1986 | Mears | 128/92 Z |

Primary Examiner—Dalton L. Truluck
Assistant Examiner—Denise Whelton
Attorney, Agent, or Firm—Peter C. Richardson; Lawrence C. Akers; Elizabeth O. Slade

[57] ABSTRACT

A device comprises two jaws arranged to be pressed one against the other and to grasp a part to be positioned and secured. The part and/or the jaws comprise circular regions presenting a succession of planar or curved facets regularly disposed over said regions, with adjacent facets forming obtuse angles between them whose vertices define sharp edges or points. In a preferred embodiment, the jaws clamping a part having a rounded portion are tightened by means of two screws whose centerlines form an angle with each other, so that upon tightening of the jaws, at least one of the jaws flexes so as to assure a better grip of the rounded portion of the part.

20 Claims, 3 Drawing Sheets

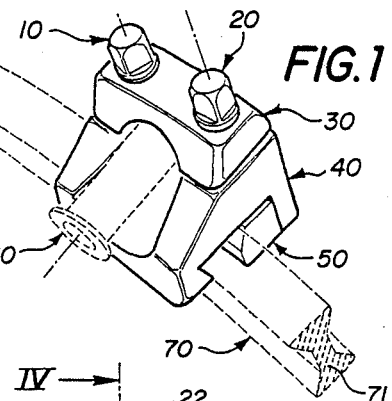
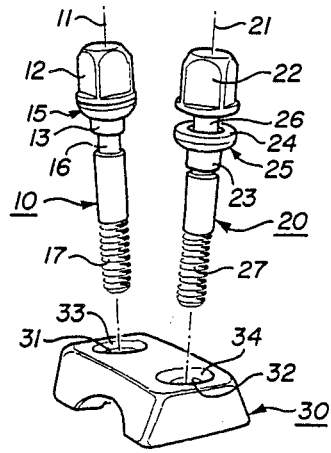
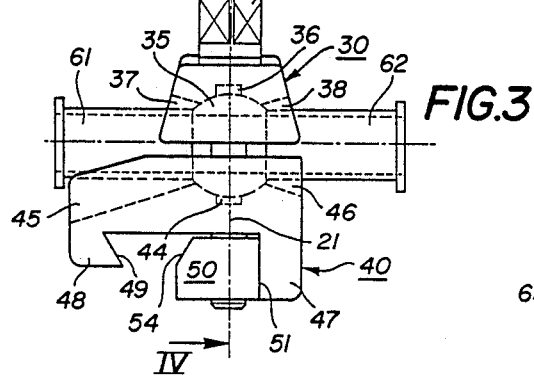
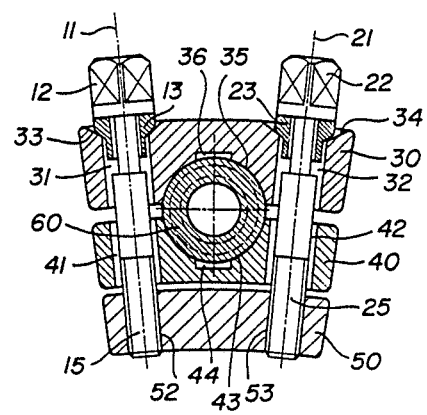
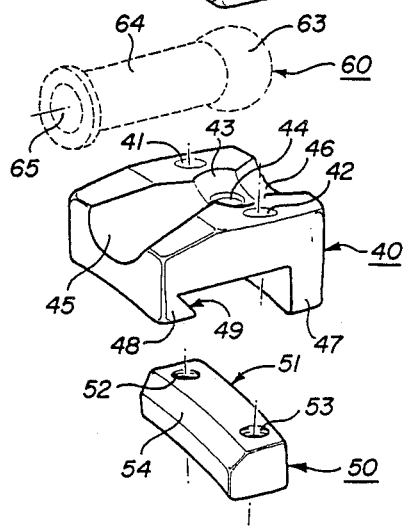

4,941,481

DEVICE FOR POSITIONING AND SECURING A PART HAVING CIRCULAR REGIONS

BACKGROUND OF THE INVENTION

The present invention relates to a fixation device permitting the orientation of the part held, which device is more specifically used in the field of external bone fixation appliances.

For the reduction of bone fractures, for example, a technique of fixing pins in the bone was in fact developed long ago, which pins are either extended in the neighboring bone or are secured in an external fixation device including a frame in order to hold the fractured segments in place.

Frame appliances comprising arcuate cradle elements are known, such as the ones described in U.S. Pat. No. 4,365,624.

The sectional shape of such an arcuate element has also been analyzed, and preference given to a form described in U.S. patent application Ser. No. 821,671, filed Jan. 23, 1986, which form permits the realization of numerous and extensive possibilities for mounting pins as well as frame rods or other connecting parts or members.

The elements of which such external fixation means are composed must be designed with two aims. Firstly, they must be as simple as possible to facilitate the surgeon's work during the operation while permitting a wide range of possible positionings. Secondly, they must afford a thoroughly rigid and secure fixation, so that the reduction of the fracture will not be compromised during convalescence.

There are known positioning and securing devices comprising jaws clamping a part, the contacting surfaces of the jaws and of the part to be clamped therewith being realized so as to be somewhat roughened, for example as obtained by sandblasting. These devices are generally satisfactory, but with time the rough surfaces wear smooth and the roughness is lost. As the surfaces in contact become smoother, the clamping becomes less and less effective.

Securing devices have also been proposed that comprise planar surfaces with grooves. Such plane surfaces commonly clamp a cylinder or a sphere of plastic material. Alternatively, grooves may likewise be provided on the part having a rounded portion to be clamped. Such a device is described, for example, in PCT World Patent Application No. 83/02554. This device gives good results, but the plastic part deteriorates quickly so that its service life is relatively short.

SUMMARY OF THE INVENTION

The object of the present invention is to eliminate these disadvantages and to provide an effective positioning and securing device having a relatively long service life.

The positioning and securing device according to the invention comprises two jaws arranged to be pressed one against the other to clamp the part. The device is characterized in that the part and/or the jaws comprise circular regions presenting a succession of planar or curved facets in regular disposition thereon, with adjacent facets forming obtuse angles between them whose vertices define sharp edges or points.

The part also includes a central bore intended to receive a rod or pin. It may be divided into two portions along the axis of the central bore, or it may be an integral part with a tube extending from the sphere, either on only one side or on both sides thereof.

Moreover, the part to be clamped may take the form of a cylinder or a truncated cone having at least one segment or region provided with facets. The cylinder to be clamped may also include a central bore perpendicular to its axis intended to receive a pin or rod and to be divided into two parts along the axis of the central bore.

The succession of facets is provided on a harder material than the material of the jaws clamping the faceted areas. These materials may be, respectively, tempered steel and untempered steel, or steel and a light metal, or light metal alloys of different hardnesses, or alloys and plastic materials.

According to a preferred embodiment, the jaws clamping the part having a rounded portion are tightened by means of two screws whose centerlines form an angle with each other, so that by tightening of the jaws, at least one of the elements bends to assure a better grip of the rounded portion of the part.

DETAILED DESCRIPTION OF THE INVENTION

The accompanying drawings, by way of example, show several embodiments and modifications of a device for positioning and securing a part according to the invention.

In the drawings:

FIG. 1 is a perspective view of a positioning and securing device intended to be placed on a circular arcuate cradle element (shown in dotted lines) and holding a guide sleeve (likewise shown in dotted lines) including a tubular portion issuing from a central sphere;

FIG. 2 is an exploded perspective view of the elements shown in FIG. 1;

FIG. 3 is a side elevation view of the device previously shown, except that in this case a sleeve having a tubular portion extending to either side of the central sphere is shown;

FIG. 4 is a sectional view taken along line IV—IV in FIG. 3;

Figure 5:
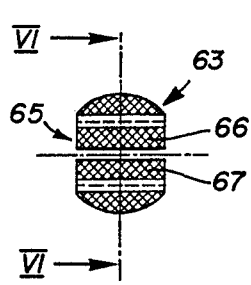
FIG. 5 is a side elevation view of a spherical sleeve.

The positioning and securing device shown in FIGS. 1 to 4 comprises principally two fixation screws 10 and 20 intended to pass through an upper member 30 and a lower member 40 and then cooperate with a shackle 50, all serving to permit the positioning and the fixation of a sleeve 60 as well as the clamping of the assembly to an arcuate element 70.

It should first be noted that the centerlines 11 and 21 of the fixation screws 10 and 20 are not parallel, but form an angle of about 10° for a reason to be explained below.

The screws 10 and 20 have large heads 12 and 22 to facilitate their placement and manual tightening before they are firmly tightened with a suitable tool when the system is in place. The depicted screws have square heads 12 and 22, but obviously any other head shape may be adopted without departing from the scope of the present invention.

Moreover, the screws 10 and 20 include washers 13 and 23 each presenting a plane face 14, 24 intended to bear against the corresponding screw head 12, 22, as well as a spherical portion 15, 25 on the opposed face, the function of which will be stated below. It is to be noted that the washers 13 and 23 are engaged with the screws 10 and 20 once and for all, and then turned in at their base into recesses 16 and 26 in the screws 10 and 20. Thus the washers 13 and 23 remain integral with the screws 10 and 20 during operations such as assembling or sterilization. In FIG. 2, washer 13 is shown against the screw head 12 to reveal the recess 16, whereas washer 23 is substantially within the lower portion of the recess 26.

The screws 10 and 20 further comprise a threaded length 17 and 27, respectively, intended to fit into a corresponding tapped hole, as will be seen below.

The screws 10 and 20 and their washers 13 and 23 are typically made of stainless steel, which affords parts that are resistant and suitable for sterilization.

The upper member 20 includes two passages 31 and 32 on the centerlines 11 and 21 for the screws 10 and 20, with the upper portion of the passages being countersunk at 33 and 34 to cooperate with the spherical face 15 or 25 of the washers 13 and 23. The concavities 33 and 34 may be either spherical or conical. To avoid any risk of cracking, the surfaces of the spherical portions 15 and 25 of the washers, as well as those of the recesses 33 and 34, should be highly polished.

The bottom face of the member 30 further includes a socket 35 centered between the passages 31 and 32, as is seen in FIG. 4. The socket 35 is provided with a central recess 36, the use of which will be explained below.

The securing member 30 is further provided with lateral relieved regions 37 and 38 on either side of the socket 35 to permit angular orientation of the tubular extensions 61 and 62 of the sleeve 60 shown in FIG. 3.

The lower member 40 faces the upper member 30 described above. It is similarly provided with two passages 41 and 42 on the centerlines 11 and 21 of the screws 10 and 20, a socket 43 with a central recess 44, and two lateral relieved regions 45 and 46, all of these features being visible either in perspective in FIG. 2 or in the side view of FIG. 3.

In its lower portion the member 40 further comprises a support extension 47 and a jaw 48 presenting an inclined face 49, which are visible in FIG. 3 especially.

The extension 47 serves as a support surface for the face 51 of the shackle 50, in which tapped holes 52 and 53 are provided on the centerlines 11 and 21 to accommodate the threads 17 and 27 of screws 10 and 20.

In the embodiment being described, where the device is mounted on an arcuate member of cross section 71 formed of two triangles joined by a web (see FIG. 1), the shackle 50 is provided with an inclined jaw 54, with the arcuate member 70 intended to be held between the jaw 48 of the lower clamp member 40 and said jaw 54.

As has just been noted, the embodiment being described relates to a device intended to be mounted on an arcuate member. For this reason the elements 30, 40 and 50 have a slight curvature, seen especially in FIG. 4, which matches the curvature of the arcuate element on which the device is mounted. Needless to say, in other embodiments the clamping elements 30 and 40, as well as the shackle 50 (if present), will be flat and not curved.

Moreover, the positioning and securing device here represented is intended to be clamped on the outside of the arcuate member, but without departing from the scope of the present invention one could of course likewise make a device intended to be placed on the inside of the arcuate member.

The clamping elements 30 and 40 as well as the shackle 50 are typically made of light alloy, but could alternatively be made of a synthetic material suitable for sterilization.

As for the spherical sleeve 60 intended to be gripped between elements 30 and 40, it may include two tubular extensions 61 and 62, as shown in FIG. 3, disposed on either side of the sphere 63. In the modification of FIGS. 1 and 2, only one lateral extension 64 is provided, the central bore 65 of which serves to guide a frame rod or other connecting piece or member.

In the modification detailed in FIG. 5, the sleeve consists wholly of a spherical portion 63. Note the small facets in this figure which, although present, are not shown in FIGS. 1 and 2 for clarity of presentation.

The sleeves of FIGS. 5 and 6 consists of two shells 66 and 67, each of which includes a trough 68 or 69. These troughs are dimensioned to clasp a fixation rod or a transcutaneous pin placed in the central passage 65 and secure it against movement in its longitudinal direction as well as in rotation.

Figure 6A:
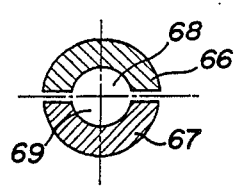
FIGS. 6A and 6B are sectional views of the sleeve of FIG. 5, in different embodiments.

In the modification of FIG. 6A, the trough 68 formed in each half shell 66 or 67 has the cross sectional shape of a semicircle.

Figure 6B:
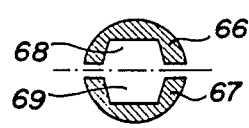
Figure 7:
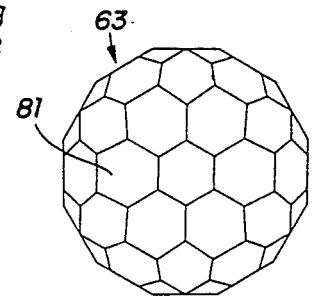
FIG. 7 is a side view of a modification of the sleeve.

Alternatively, the trough 69 may have a cross section in the form of a regular trapezoid, in which the inclined sides form an angle greater than or equal to 7° with the perpendicular to the two other sides, as is seen in FIG. 6B. The exterior of the spherical sleeve 63 represented in FIG. 7 consists of hexagonal facets; needless to say, the use of other polygons is likewise contemplated.

Figure 8:
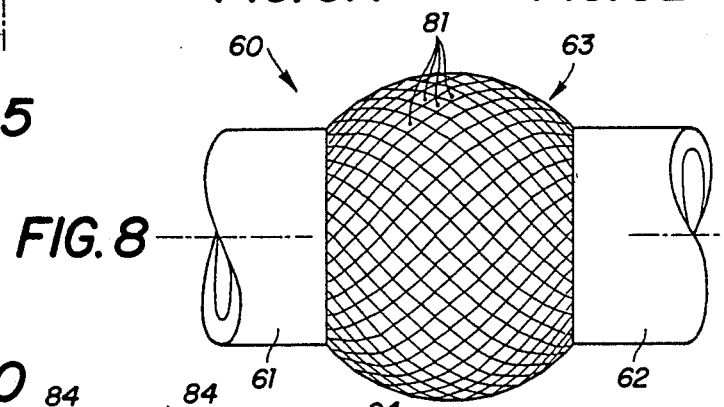
FIG. 8 is an enlarged view of the central portion of the sleeve of FIG. 3, showing facets regularly arrayed over the surface of the spherical portion.

FIG. 8 depicts the central portion of the sleeve 60 shown in FIG. 3 having tubular extensions 61 and 62 disposed on either side of the sphere 63, said central portion being much enlarged. Note the succession of small facets 81, regularly spaced and disposed upon the surface of the sleeve.

Figure 9:
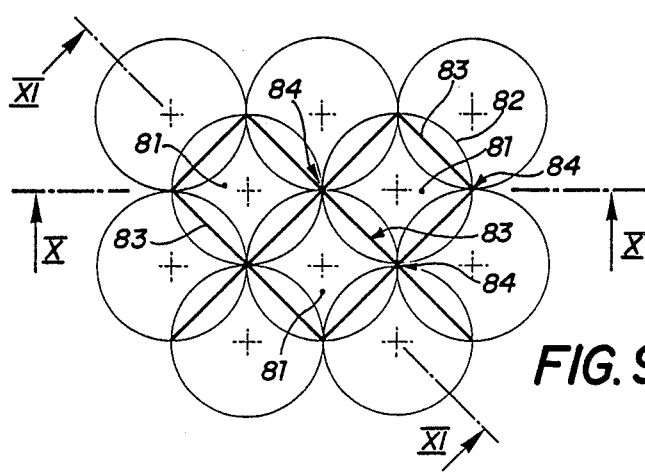
FIG. 9 is a further enlarged view of a small portion of the surface of the sleeve represented in FIG. 8, showing the facets in detail, in a first embodiment having planar facets.

An enlarged detail of the facets 81 is presented in FIG. 9, which shows that the facets 81 are inscribed in adjacent circles 82, with each set of circles having at its center another circle of the same diameter intersecting the other four circles so as to define sharp edges 83 as well as the corners 84 of the facets 81. Preferably, the circles 82 are of such a size that the corners 84 of a single facet are inscribed in an angle of about 10° from the center of the sphere 63.

Figure 10:
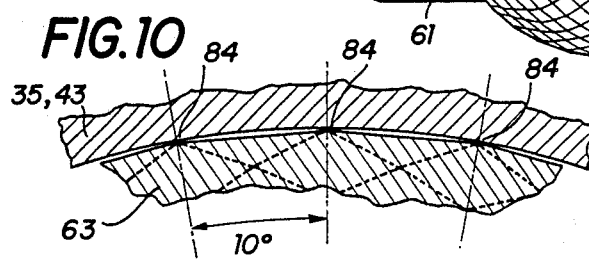
FIG. 10 is a sectional view taken along line X—X in FIG. 9, showing also a portion of the jaw.

The cross sectional view of FIG. 10, along the line X—X in FIG. 9, is taken so as to intersect all the common corners 84 of successive facets in a row of facets 81. Thus each corner 84 is a point that will come into contact with the sockets 35 and 43 of clamping members 30 and 40.

Figure 11:
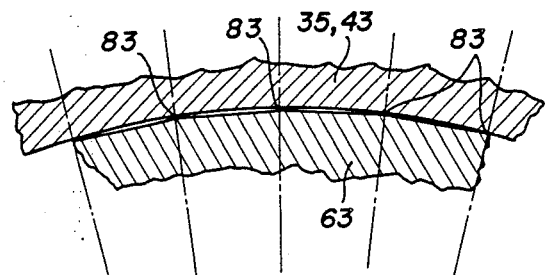
FIG. 11 is a sectional view taken along line XI—XI in FIG. 9, likewise including a portion of the jaw.

The cross sectional view of FIG. 11, along XI—XI in FIG. 9, is taken so as to intersect the sharp edges 83 perpendicularly.

Figure 12:
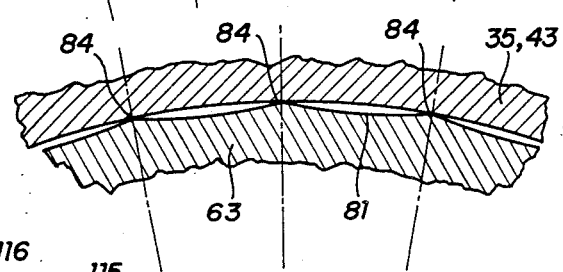
FIG. 12 is similar to FIG. 10, but in a second embodiment having concave facets.

Whereas in FIGS. 9 to 11, corresponding to a first embodiment, the facets are planes, in the modification of FIG. 12 (which corresponds to FIG. 11) the facets 81 are curved. As a result, sharper vertices 84 are obtained which are hence more effectively secured in the sockets 35 and 43 of the jaws 30 and 40.

Furthermore, it will be clear to those skilled in the art that the facets may be of other polygonal shapes. The purpose of the presence of the facets, planar or curved, may be stated as being to create sharp edges or points between the facets, permitting a firm grip with the jaws.

The sleeve part 60 is in general intended to be traversed by and to retain pins or rods of from 2 to 8 mm. in diameter. Hence the spherical portion 63 will typically be from 15 to 20 mm. in diameter.

As a general rule, the jaws 30 and 40 will be made of a material having a lower hardness than the material of the sleeve 60. Thus the enclosure formed by the jaws will be more elastic than the portion 63 of the sleeve. On that basis, a large number of materials may be chosen. For example, the sleeve 60 may be of tempered steel and the jaws of untempered steel. Alternatively, a steel sleeve may be associated with jaws of light alloy, or a sleeve of light alloy with jaws having a lower hardness, for example of plastic material.

The use of the positioning and securing device represented in FIGS. 1 to 4 will now be described in detail.

In each case, the type of sleeve 60 required in the assembly will first be determined, whether a sleeve with two lateral extensions 61 and 62 (see FIG. 3), or a sleeve with one extension 64 (FIG. 2), or a simple spherical sleeve, possibly composed of two hemispherical shells 66 and 67 (FIG. 5).

The diameter of the central bore 65 will be chosen according to the pieces to be assembled.

The assembly will then be mounted directly on the arcuate element, without of course yet firmly tightening the screws 10 and 20 in the corresponding tapped holes 52 and 53 of piece 50, and the spherical part 60 as well as the arcuate element 70 are disposed according to requirements.

One now appreciates the function of the lateral clearances 37 and 38 of member 30, and 45 and 46 of member 40, which allow the tubular portions 64, or 61 and 62, to be oriented, unrestricted by the members 30 and 40, within a range of angular orientation of up to about 40°.

When the proper positioning has been attained, the screws 10 and 20 can be tightened so as to lock the assembly, which may of course be unlocked subsequently at any time to permit any adjustment.

Upon recalling that the centerlines 11 and 21 are not strictly parallel, but form a mutual angle of about 10°, it will be appreciated how the invention affords an improved security, both of the sleeve and of the arcuate member, since the tightening of the screws can flex the clamping members 30 and 40.

The deformation due to the flexure of members 30 and/or 40 is compensated for by the play of the washers 13 and 23, whose spherical portion 15 or 25 rests in the spherical or conical sockets 33 and 34. These washers serve to augment clasping while reducing friction. In practice, the spherical portions 15 and 25 of the washers should be dimensioned so that contact with the corresponding socket occurs approximately at the center of the rounded portion.

It should also be noted that the recesses 36 and 44 of the clamping members 30 and 40, respectively, serve to increase the elasticity of members 30 and 40 and hence enhance the clamping, since they allow for duplication of the fulcrum on the spherical portion of the sleeve.

Figure 14:
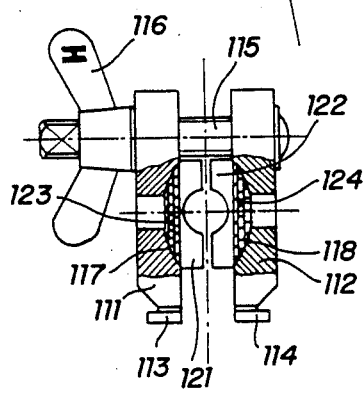
FIG. 14 is a side view of the device of FIG. 13 intended to position and secure a connecting bar, with the upper portion of the jaws shown partially in section.
Figure 13:
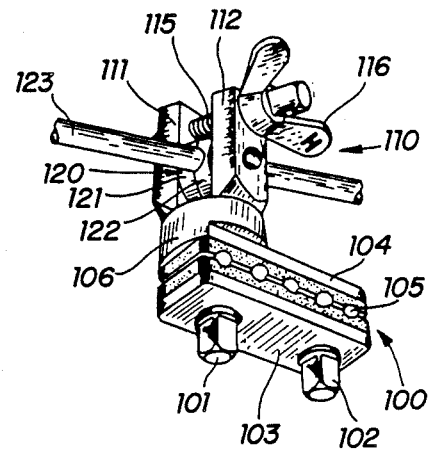
FIG. 13 is a perspective view of a positioning and securing device intended to receive transfixing pins.
Figure 15:
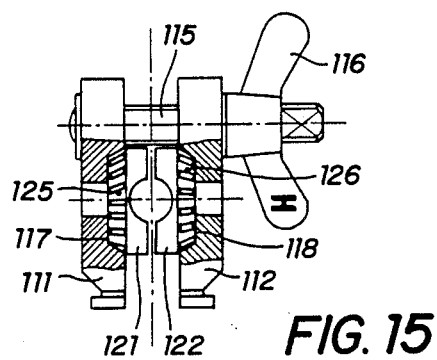
FIG. 15 is a side view of a modification of the part shown in FIG. 14.

FIGS. 13 to 15 depict a second embodiment of a positioning and securing device, likewise used in an external fixation apparatus. This device consists chiefly of a fixation assembly 100 and a positioning and clamping member 110.

The fixation assembly 100 is intended to be clamped upon several transfixing pins by means of screws 101 and 102, and for this purpose the jaws 103 and 104 define passages 105 intended to clamp the transfixing pins (not shown in the drawings).

This fixation assembly 100 for transfixing pins further comprises a cylindrical portion 106 having an internal circular groove (not shown), intended to cooperate with the clamping member 110.

For this purpose, the member 110 comprises two clamp parts 111 and 112 whose lower portions have feet 113 and 114 adapted to be engaged in the inner circular groove of cylinder 106. The clamp parts 111 and 112 are traversed at their upper end by a threaded rod 115 engaged with a wing nut 116. Parts 111 and 112 retain a sleeve 120 consisting of two circular pieces 121 and 122 (FIG. 14) which retain themselves a rod 123 in a bore common to the two pieces 121 and 122. As in the preceding version, this bore may be polygonal in cross section.

When pieces 111 and 112 are tightened under the action of the nut 116, feet 113 and 114 will bear firmly against the groove in portion 106 and prevent rotation of the upper assembly 110. The clamp parts 111, 112 have circular surfaces 117, 118 placed facing one another, against which the circular surfaces 123, 124 of the cylindrical pieces 121 and 122 will come to bear. These surfaces 123, 124 present rows of rectangular facets forming sharp edges between them. In the embodiment of FIG. 14, the rows of facets are arrayed along spherical segments or zones dividing the domes of the lateral portions of the pieces 121, 122. In this case the facets are planar facets made of a harder material than the material forming parts 111, 112.

In the modification of FIG. 15, parts 111, 112 are included again having the same configuration as the parts in FIG. 14, except that the inner surfaces 117, 118 have the form of a truncated conical bore. The circular pieces 121, 122 intended to clamp the rod 123 likewise have truncated conical lateral portions 125, 126, which present a succession of rectangular facets arrayed along the generatrices of the truncated conical portions. The facets form sharp edges between them which will come to bear against the corresponding smooth portions, having the shape of a truncated cone, of the parts 111, 112. As in the previous embodiments or modifications, the pieces 121, 122 will be made of a harder material than the parts 111, 112.

The embodiments and modifications described herein propose a positioning and securing means for a part with the aid of jaws affording a far better effectiveness of clamping than anything known to date in the prior art. This effective clamping is obtained by providing a succession of plane or curved facets on the part to be clamped, arranged over areas of the part to be clamped in such a manner that adjacent facets form sharp edges or points between them. The part to be clamped and secured comprising the facets is made of a harder material than that of the jaws. This enables the sharp edges or points formed by the facets to produce elastic deformations in the jaws, thereby providing an especially effective clamping effect. It will be clear to those skilled in the art that the facets may instead be provided on the jaws, and in that case the jaws would be made of a harder material than that provided for the part to be clamped.

I claim:

1. A system comprising a part to be positioned and secured and a device for positioning and securing said part, said device comprising two jaws arranged to be pressed against each other to clamp said part, wherein at least one element selected from the group consisting of said part and said jaws comprises at least one region, the cross-section of which is circular, wherein said at least one region has a succession of facets regularly arrayed over at least a portion of said at least one region, wherein adjacent facets meet at obtuse angles and wherein the boundaries between adjacent facets are sharp edges or sharp points, wherein said at least one region is located on said part to be positioned and secured, wherein the surfaces of the jaws in contact with said part are smooth, and wherein said part to be positioned and secured comprises a sphere having at least one faceted segment, and wherein said sphere includes a central bore intended to receive a rod.

2. A system of claim 1 wherein said sphere is divided into two parts along the axis of the central bore.

3. A system of claim 1 wherein said sphere is integral with a tube extending said bore on both sides of the sphere.

4. A system, comprising a part to be positioned and secured and a device for positioning and securing said part, said device comprising two jaws arranged to be pressed against each other to clamp said part, wherein at least one element selected from the group consisting of said part and said jaws comprises at least one region, the cross-section of which is circular, wherein said at least one region has a succession of facets regularly arrayed over at least a portion of said at least one region, wherein adjacent facets meet at obtuse angles and wherein the boundaries between adjacent facets are sharp edges or sharp points, wherein said part has the form of a cylinder having at least one faceted region, wherein said cylinder includes a central bore parallel to the axis of said cylinder, and wherein the cylinder is divided into two parts along the axis of the central bore.

5. A device for positioning and securing at least one part having a rounded portion, said device comprising two members which are adapted to be disposed facing one another and which firmly clamp said part between said members, wherein said members are capable of being pressed together by at least two screws whose centerlines are not strictly parallel, so that upon tightening of said screws at least one of said members flexes so as to more firmly secure the rounded portion of said part.

6. A device of claim 5 wherein said members comprise an upper clamp, a lower clamp, and a shackle, with said screws passing freely through the upper and lower clamps, the heads of said screws being adapted to rest at least indirectly on the upper clamp and the threaded ends of said screws being adapted to cooperate with matching tapped holes provided in said shackle.

7. A device of claim 6 wherein said shackle is linked in use with one of said clamping members.

8. A device of claim 6 wherein the head of each of said screws cooperates with a washer allowing compensation for the flexure of at least one of said members.

9. A device of claim 8 wherein each washer includes a spherical portion and the upper clamp is provided with a recess adapted to cooperate with said spherical portion.

10. A device of claim 9 wherein each of said recesses is hemispherical.

11. A device of claim 8 wherein each washer is crimped into a recess provided on the midportion of the associated screw so as to remain integral with the screw and wherein the angle between said centerlines is about 10°.

12. A device of claim 5 wherein each of the members surrounding said part includes a rounded portion having a socket corresponding to the shape of said part.

13. A device of claim 12 wherein each of said sockets is centered in the plane passing through the fixation screws.

14. A device of claim 12 wherein said socket is provided with at least one recess intended to increase the elasticity of the member.

15. A device of claim 12 wherein said socket communicates with a pair of clearances located on either side of the plane passing through the fixation screws, which clearances permit angular movement of said part to be positioned and secured, when said part is a sleeve having at least one lateral extension.

16. A device of claim 12 wherein the spherical portion of each of the sockets has a surface at least a part of which is adapted to improve the clamping effect.

17. A device of claim 16 wherein said surface is provided with a succession of regularly arrayed facets, wherein adjacent facets meet at obtuse angles and wherein the boundaries between adjacent facets are sharp edges or sharp points.

18. A device of claim 6 wherein the lower clamping member and the shackle are shaped so as each to form a jaw of a vise to permit their fixation on a frame of a skeletal fixation appliance.

19. A device of claim 18 wherein said frame is constituted at least in part by an arcuate cradle part, and said upper and lower clamping members and said shackle have a curvature matching that of said arcuate part.

20. A device of claim 9 wherein each of said recesses is conical.

* * * * *